United States Patent [19]

Vernieres et al.

[11] Patent Number: 4,788,188

[45] Date of Patent: Nov. 29, 1988

[54] QUINOLYLGLYCINAMIDE DERIVATIVES, THE PROCESS FOR PREPARATION THEREOF AND THEIR THERAPEUTIC APPLICATION AS PSYCHOTROPIC DRUGS

[75] Inventors: Jean-Claude Vernieres, Muret; Etienne Mendes, Toulouse; Michel Morre, Toulouse; Peter Keane, Toulouse; Jacques Simiand, Muret, all of France

[73] Assignee: Sanofi (S.A.), France

[21] Appl. No.: 860,051

[22] Filed: May 6, 1986

[30] Foreign Application Priority Data

May 6, 1985 [FR] France ................... 85 07247

[51] Int. Cl.$^4$ ............... C07D 215/54; C07D 215/02; C07D 401/12; A61K 31/47
[52] U.S. Cl. ................... 514/212; 514/313; 514/235.2; 544/128; 544/168; 546/162; 546/170; 540/597
[58] Field of Search ............ 514/212, 313; 540/597; 546/159, 162

[56] References Cited

U.S. PATENT DOCUMENTS

| | | | |
|---|---|---|---|
| 2,456,911 | 12/1948 | Bruce | 546/171 |
| 3,470,186 | 9/1969 | Hanifin | 546/160 |
| 3,769,410 | 10/1973 | Bertrand | 514/313 |

*Primary Examiner*—Donald G. Daus
*Assistant Examiner*—F. Bernhardt
*Attorney, Agent, or Firm*—Wegner & Bretschneider

[57] ABSTRACT

The present invention relates to new quinolylglycinamide derivatives corresponding to the following general formula:

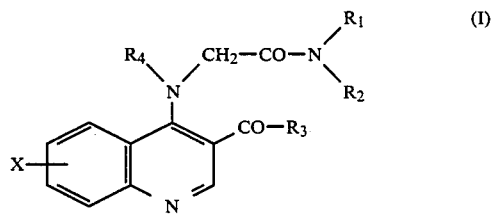

The invention also relates to a process for preparing these compounds and their therapeutic application as a psychotropic agent.

10 Claims, No Drawings

QUINOLYLGLYCINAMIDE DERIVATIVES, THE PROCESS FOR PREPARATION THEREOF AND THEIR THERAPEUTIC APPLICATION AS PSYCHOTROPIC DRUGS

The present invention relates to new quinolyl glycinamide derivatives, the process for preparation thereof and their therapeutic application as psychotropic drugs.

The compounds of the invention correspond to the following general formula:

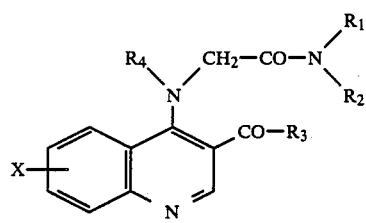

in which $R_1$ and $R_2$ each denote, independently of each other, a hydrogen or a lower alkyl radical or alternatively, when $R_1$ is an alkyl radical, $R_2$ can denote a cycloalkyl radical or an optionally substituted phenyl or benzyl radical or, as a further alternative, $R_1$ and $R_2$ can form with the nitrogen atom to which they are attached a heterocyclic system capable of containing a second heteroatom such as oxygen, sulphur or nitrogen;

$R_3$ denotes a hydrogen, a hydroxyl OH, a lower alkyl or alkoxy group or an optionally substituted phenoxy or benzyloxy group, or alternatively $R_3$ denotes a group $-NH-R_5$, in which $R_5$ is a hydrogen or a lower alkyl or a phenyl radical;

$R_4$ denotes hydrogen or a lower alkyl radical;

X denotes a hydrogen or a halogen atom, a lower alkyl radical or a cycloalkyl, alkoxy, nitro, trifluoromethyl or methylthio radical.

The invention also relates to the addition salts with pharmaceutically acceptable inorganic or organic acids and, where appropriate, when $R_3$ denotes OH, the salts with pharmaceutically acceptable alkali metal bases NaOH or KOH) or organic bases (piperazine, lysine or morpholine).

A lower alkyl or alkoxy radical is understood to mean a saturated or unsaturated linear or branched $C_1$-$C_4$ hydrocarbon radical. A heterocyclic system particularly comprises a pyrrolidino, piperidino, homopiperidino (hexamethyleneimino) or morpholino- radical, optionally substituted with a lower alkyl radical.

The subject of the invention is also a process for preparing the compounds of formula (I), characterized in that a glycine derivative of formula

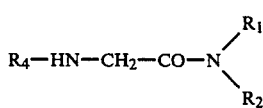

in which $R_1$, $R_2$ and $R_4$ are as defined above, is reacted with a 4-chloroquinoline of formula

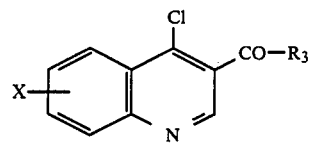

in which X and $R_3$ have the meanings defined above.

The condensation reaction is performed by heating the two reagents to a temperature of between 60° C. and 130° C. in the presence of an organic base such as triethylamine or an inorganic base such as sodium carbonate. This reaction is advantageously carried out in an organic solvent such as toluene, ethyl alcohol or isopropyl alcohol.

The compounds of formula (I) in which $R_3$ denotes OH can also be obtained by saponification, in sodium hydroxide or potassium hydroxide, of the esters of formula (I) in which $R_3$ is an alkoxy group, or by hydrogenation, in the presence of catalysts, of the esters of formula (I) in which $R_3$ is a benzyloxy group.

The glycine derivatives of formula (II), which are known compounds, have been prepared by 3 methods:

(a) when $R_4$ is hydrogen, the derivatives are obtained in the form of the hydrochloride (R. D. HAWORTH et al., J. Chem. Soc., 1952, 2972-2980) according to the following scheme:

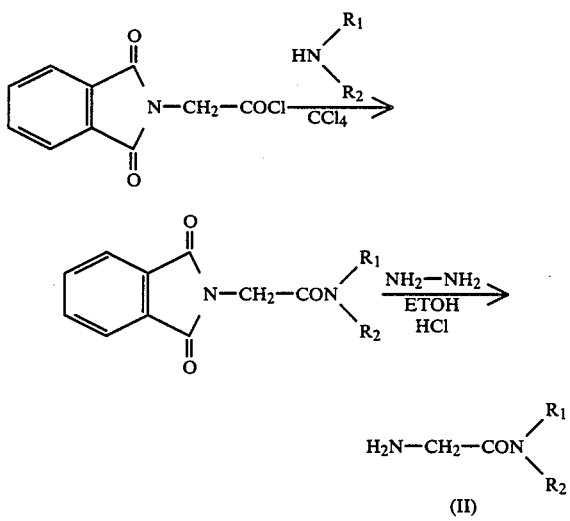

(b) when $R_4$ is a methyl group, the derivatives of formula (II) are prepared from sarcosine esters of formula

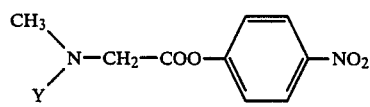

Y being a protective group, denoting either a benzyloxycarbonyl group of formula

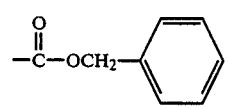

(A. B. MAUGER and R. WADE, J. Chem.

-continued
Soc., 1965, 3126–3132)

or a tert-butyloxycarbonyl group,

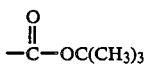

(Chem. Abstracts, 1970, 73, 56417 r).

By treating these esters with amines of formula

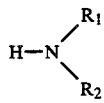

amides of formula

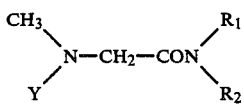

are obtained and then, after removal of the protective group Y, the derivative of formula

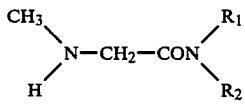

(c) by treating chloroacetyl chloride first with an amine of formula

and then with an amine of the type $H_2N-R_4$ $$Cl-CH_2-COCl \xrightarrow{HN\begin{smallmatrix}R_1\\R_2\end{smallmatrix}} Cl-CH_2-CON\begin{smallmatrix}R_1\\R_2\end{smallmatrix} \xrightarrow{H_2N-R_4}$$

$$\begin{smallmatrix}R_4\\H\end{smallmatrix}N-CH_2-CON\begin{smallmatrix}R_1\\R_2\end{smallmatrix}$$

The derivatives of formula (III), 4-chloroquinolines, are known compounds. Thus, C. E. KASLOW and W. R. CLARK (J. Org. Chem., 1953, 18, 55–58), J. W. HANIFIN et al. (J. Med. Chem., 1969, 12, 1096–1097) and E. H. ERICKSON et al. (J. Med. Chem. 1979, 22, 816–823) have described 4-chloro-3-ethoxycarbonyl-quinolines; and C. C. PRICE et al. (J.A.C.S., 1946, 68, 1251–1252) and C. J. OHNMACHT et al. (J. Med. Chem., 1971, 14, 17–24) have described 3-chlorocarbonyl-4-chloroquinolines of formula

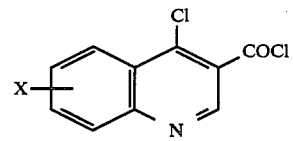

which, by means of classical reactions with alcohols or amines, enable the desired derivative of formula (III) to be obtained.

The following non-limitative examples illustrate the invention:

Example 1

2-(3-Ethoxycarbonyl-6-chloro-4-quinolyl)amino-N,N-diethylacetamide; derivative No. 1 ($R_1=R_2=C_2H_5$; $R_3=OC_2H_5$; $R_4=H$, $X=Cl$).

A mixture of ethyl 4,6-dichloroquinoline-3-carboxylate (4 g; 0.016 mol), 2-amino-N,N-diethylacetamide hydrochloride (2.9 g; 0.0176 mol), prepared according to R. D. HAWORTH et al. (J. Chem. Soc., 1952, 2972–80) and triethylamine (4.9 ml; 0.0352 mol) in ethanol (40 ml) is brought to reflux for 5 hours under nitrogen. After evaporation of the solvent, the crystals obtained are solubilized in dichloromethane. The solution is washed with water and dried over sodium sulphate, and the solvent is evaporated. The expected product is recrystallized in an isopropyl ether/ethyl acetate (4:6) mixture: colourless crystals, m.p. 101° C. (yield 67%).

| Analysis: $C_{18}H_{22}N_3ClO_3$ | | | |
|---|---|---|---|
| Calculated: | C, 59.42 | H, 6.09 | N, 11.55 |
| Found: | C, 59.31 | H 6.05 | N, 11.63 |

The maleate of this compound was prepared. Colourless crystals are obtained.

M.p. 147° C. (yield 50%).

| Analysis: $C_{22}H_{26}ClN_3O_7$ | | | |
|---|---|---|---|
| Calculated: | C, 55.06 | H, 5.46 | N, 8.76 |
| Found: | C, 55.09 | H, 5.60 | N, 8.56 |

Example 2

2-[(3-Ethoxycarbonyl-6-methyl)-4-quinolyl]amino-N,N-diethylacetamide hydrochloride; derivative No. 2 ($R_1=R_2=C_2H_5$; $R_3=O_2H_5$; $R_4=H$; $X=CH_5$)

2.49 g (0.01 mol) of ethyl 6-methyl-4-chloroquinoline-3-carboxylate, 1.85 g (0.011 mol) of 2-amino-N,N-diethylacetamide, 3.1 ml (0.022 mol) of triethylamine and 20 ml of absolute ethanol are brought to reflux for 15 hours. When the ethanol has been removed, the residue is taken up with 10 ml of water and, after extraction with dichloromethane, the organic phase is then washed with the minimum amount of water, dried and concentrated. The hydrochloride is recrystallized in isopropanol: colourless crystals, m.p. >260° C. (yield 50%).

| Analysis: $C_{19}H_{25}N_3O_3HCl$ | | | |
|---|---|---|---|
| Calculated: | C, 60.07 | H, 6.90 | N, 11.06 |
| Found: | C, 60.27 | H, 6.87 | N, 10.88 |

Following the procedure described in Example 1, the following compounds of Examples 3 to 11 were successively prepared from 4-chloroquinolines variously substituted in position 6 and 2-amino-N,N-diethylacetamide hydrochloride:

Example 3

2-(3-Ethoxycarbonyl-6-methoxy-4-quinolyl)amino-N,N-diethylacetamide; derivative No. 3 ($R_1=R_2=C_2H_5$; $R_3=OC_2H_5$; $R_4=H$; $X=OCH_3$)
M.p. 163° C. (yield 88%).

| Analysis: $C_{19}H_{25}N_3O_4$ | | | |
|---|---|---|---|
| Calculated: | C, 63.49 | H, 7.01 | N, 11.69 |
| Found: | C, 63.46 | H, 6.99 | N, 11.61 |

Example 4

2-(3-Ethoxycarbonyl-6-trifluoromethyl-4-quinolyl)amino-N,N-diethylacetamide; derivative No. 4. ($R_1=R_2=C_2H_5$; $R_3=OC_2H_5$; $R_4=H$; $X=CF_3$)
M.p.=136° C. (yield 50%).

| Analysis: $C_{19}H_{22}F_3O_3$ | | | |
|---|---|---|---|
| Calculated: | C, 57.43 | H, 5.58 | N, 10.57 |
| Found: | C, 57.31 | H, 5.66 | N 10.76 |

Example 5

2-(3-Ethoxycarbonyl-6-nitro-4-quinolyl)amino-N,N-diethylacetamide; derivative No. 5 ($R_1=R_2=C_2H_5$; $R_3=OC_2H_5$; $R_4=H$; $X=NO_2$)
M.p. 170° C. (yield 70%).

| Analysis: $C_{18}H_{22}N_4O_5$ | | | |
|---|---|---|---|
| Calculated: | C, 57.74 | H, 5.32 | N, 14.97 |
| Found: | C, 57.53 | H, 5.70 | N, 14.86 |

Example 6

2-(3-Ethoxycarbonyl-6-butyl-4-quinolyl)amino-N,N-diethylacetamide; derivative No. 6 ($R_1=R_2=C_2H_5$; $R_3=OC_2H_5$; $R_4=H$; $X=C_4H_9$)
M.p. 128° C. (yield 70%).

| Analysis: $C_{22}H_{31}N_3O_3$ | | | |
|---|---|---|---|
| Calculated: | C, 68.54 | H, 8.10 | N, 10.90 |
| Found: | C, 68.51 | H, 8.32 | N, 10.91 |

Example 7

2-(3-Ethoxycarbonyl-6-fluoro-4-quinolyl)amino-N,N-diethylacetamide; derivative No. 7. ($R_1=R_2=C_2H_5$; $R_3=OC_2H_5$; $R_4=H$, $X=F$)
M.p. 126° C. (yield 60%).

| Analysis: $C_{18}H_{22}FN_3O_3$ | | | |
|---|---|---|---|
| Calculated: | C, 62.24 | H, 6.38 | N, 12.10 |
| Found: | C, 62.00 | H, 6.30 | N, 12.03 |

Example 8

2-(3-Ethoxycarbonyl-6-methoxy-4-quinolyl)amino-N,N-diethylacetamide; derivative No 8 ($R_1=R_2=C_2H_5$; $R_3=OC_2H_5$; $R_4=H$; $X=OC_2H_5$)
M.p. 184° C. (yield 55%).

| Analysis: $C_{20}H_{27}N_3O_4$ | | | |
|---|---|---|---|
| Calculated: | C, 64.32 | H, 7.29 | N, 11.25 |
| Found: | C, 64.16 | H, 7.23 | N, 11.13 |

Example 9

2-(3-Ethoxycarbonyl-6-cyclohexyl-4-quinolyl)amino-N,N-diethylacetamide; derivative No. 9. ($R_1=R_2=C_2H_5$; $R_3=OC_2H_5$; $R_4=H$; $X=$cyclohexyl)
M.p. 130° C. (yield 60%).

| Analysis: $C_{24}H_{33}N_3O_3$ | | | |
|---|---|---|---|
| Calculated: | C, 70.04 | H, 8.08 | N, 10.21 |
| Found: | C, 70.26 | H, 8.32 | N, 9.96 |

Example 10

2-(3-Ethoxycarbonyl-4-quinolyl)amino-N,N-diethylacetamide; derivative No. 10. ($R_1=R_2=C_2H_5$; $R_3=OC_2H_5$; $R_4=H$, $X=H$)
M.p. 120° C. (yield 70%).

| Analysis: $C_{18}H_{23}N_3O_3$ | | | |
|---|---|---|---|
| Calculated: | C, 65.63 | H, 7.04 | N, 12.76 |
| Found: | C, 65.74 | H, 7.17 | N, 12.77 |

Example 11

2-(3-Ethoxycarbonyl-6-butoxy-4-quinolyl)amino-N,N-diethylacetamide; derivative No. 11. ($R_1=R_2=C_2H_5$; $R_3=OC_2H_5$; $R_4=H$; $X=OC_4H_9$)
M.p. 163° C. (yield 50%)

| Analysis: $C_{22}H_{31}N_3O_4$ | | | |
|---|---|---|---|
| Calculated: | C, 65.81 | H, 7.78 | N, 10.47 |
| Found: | C, 65.88 | H, 7.59 | N, 10.50 |

Example 12

2-(3-Ethoxycarbonyl-6-chloro-4-quinolyl)amino-N,N-dipropylacetamide; derivative No. 12. ($R_1=R_2=C_3H_7$; $R_3=OC_2H_5$; $R_4=H$; $X=Cl$)

A mixture of ethyl 4,6-dichloroquinoline-3-carboxylate (2.7 g; 0.01 mol), 2-amino-N,N-dipropylacetamide hydrochloride (2.14 g; 0.011 mol) and triethylamine (2.22 g; 0.022 mol) in ethanol (60 ml) is brought to reflux for 4 hours. After concentration of the solvent, washing with water, extraction with dichloromethane, drying over $Na_2SO_4$ and evaporation of the solvent, the expected product is recrystallized in a cyclohexane/ethyl acetate (90:10) mixture: beige crystals, m.p. 116° C. (yield 60%).

| Analysis: $C_{20}H_{26}ClN_3O_3$ | | | |
|---|---|---|---|
| Calculated: | C, 61.30 | H, 6.69 | N, 10.72 |

-continued

| Analysis: $C_{20}H_{26}ClN_3O_3$ | | | |
|---|---|---|---|
| Found: | C, 61.10 | H, 6.40 | N, 10.86 |

The phosphate and the sulphate of this compound were prepared. By way of example, the hydrated acid sulphate of Example 12 was obtained: colourless crystals, m.p. 150° C.

| Analysis: $C_{20}H_{28}ClN_3O_7S$, $\frac{1}{2}H_2O$ | | | |
|---|---|---|---|
| Calculated: | C, 48.13 | H, 5.85 | N, 8.41 |
| Found: | C, 47.90 | H, 5.56 | N, 8.36 |

Following the procedure described in Example 12, the following compounds of Examples 13 to 20 were successively prepared from 2-amino-N,N-dipropylacetamide hydrochloride:

Example 13

2-(3-Ethoxycarbonyl-6-methyl-4-quinolyl)amino-N,N-dipropylacetamide hydrochloride; derivative No. 13. ($R_1=R_2=C_3H_7$; $R_3=OC_2H_5$; $R_4=H$; $X=CH_3$)

M.p. 259° C. (yield 40%).

| Analysis: $C_{21}H_{29}N_3O_3HCl$ | | | |
|---|---|---|---|
| Calculated: | C, 61.83 | H, 7.41 | N, 10.30 |
| Found: | C, 61.74 | H, 7.24 | N, 10.20 |

Example 14

2-(3-Ethoxycarbonyl-6-methoxy-4-quinolyl)amino-N,N-dipropylacetamide; derivative No. 14. ($R_1=R_2=C_3H_7$; $R_3=OC_2H_5$; $R_4=H$, $X=OCH_3$)

M.p. 163° C. (yield 70%).

| Analysis: $C_{21}H_{29}N_3O_4$ | | | |
|---|---|---|---|
| Calculated: | C, 65.09 | H, 7.54 | N, 10.84 |
| Found: | C, 65.11 | H, 7.65 | N, 10.82 |

Example 15

2-(3-Ethoxycarbonyl-4-quinolyl)amino-N,N-dipropylacetamide; derivative No. 15. ($R_1=R_2=C_3H_7$; $R_3=OC_2H_5$; $R_4H$; $X=H$)

M.p. 120° C. (yield 60%).

| Analysis: $C_{20}H_{27}N_3O_3$ | | | |
|---|---|---|---|
| Calculated: | C, 67.20 | H, 7.61 | N, 11.76 |
| Found: | C, 67.31 | H, 7.76 | N, 11.81 |

Example 16

2-(3-Ethoxycarbonyl-6-ethoxy-4-quinolyl)amino-N,N-dipropylacetamide; derivative No. 16. ($R_1=R_2=C_3H_7$; $R_3=OC_2H_5$; $R_4=H$, $X=OC_2H_5$)

M.p. 176° C. (yield 55%).

| Analysis: $C_{22}H_{31}N_3O_4$ | | | |
|---|---|---|---|
| Calculated: | C, 65.81 | H, 7.78 | N, 10.47 |
| Found: | C, 65.73 | H, 7.94 | N, 10.26 |

Example 17

2-(3-Ethoxycarbonyl-6-bromo-4-quinolyl)amino-N,N-dipropylacetamide; derivative No. 17. ($R_1=R_2=C_3H_7$; $R_3=OC_2H_5$; $R_4=H$; $X=Br$)

M.p. 126° C. (yield 60%).

| Analysis: $C_{20}H_{26}BrN_3O_3$ | | | |
|---|---|---|---|
| Calculated: | C, 55.05 | H, 6.01 | N, 9.63 |
| Found: | C, 55.17 | H, 5.97 | N, 9.66 |

Example 18

2-(3-Ethoxycarbonyl-6-nitro-4-quinolyl)amino-N,N-dipropylacetamide; derivative No. 18. ($R_1=R_2=C_5H_7$; $R_3=OC_2H_5$; $R_4H$; $X=NO_2$)

M.p. 160° C. (yield 50%).

| Analysis: $C_{20}H_{26}N_4O_5$ | | | |
|---|---|---|---|
| Calculated: | C, 64.86 | H, 5.68 | N, 9.86 |
| Found: | C, 64.78 | H, 5.63 | N, 9.75 |

Example 19

2-(3-Ethoxycarbonyl-6-trifluoromethyl-4-quinolyl)amino-N,N-dipropylacetamide; derivative No. 19. ($R_1=R_2=C_3H_7$; $R_3=OC_2H_5$; $R_4=H$; $X=CF_3$)

M.p.=144° C. (yield 60%).

| Analysis: $C_{21}H_{26}F_3N_3O_3$ | | | |
|---|---|---|---|
| Calculated: | C, 59.28 | H, 6.16 | N, 9.87 |
| Found: | C, 58.98 | H, 5.96 | N, 9.67 |

Example 20

2-(3-Ethoxycarbonyl-6-methylthio-4-quinolyl)amino-N,N-dipropylacetamide; derivative No. 20. ($R_1=R_2=C_3H_7$; $R_3=OC_2H_5$; $R_4=H$, $X=SCH_3$)

M.p. 162° C. (yield 72%).

| Analysis: $C_{21}H_{29}N_3O_3S$ | | | |
|---|---|---|---|
| Calculated: | C, 62.50 | H, 7.24 | N, 10.41 |
| Found: | C, 62.36 | H, 7.74 | N, 10.27 |

Following the procedure described in Example 1, the following compounds of Examples 21 to 42 were prepared from variously substituted 2-aminoacetamide hydrochlorides:

Example 21

2-(3-Ethoxycarbonyl-6-chloro-4-quinolyl)amino-N,N-diisobutylacetamide; derivative No. 21. ($R_1=R_2=CH_2-CH(CH_3)_2$; $R_3=OC_2H_5$; $R_4=H$; $X=Cl$)

M.p. 136° C. (yield 50%).

| Analysis: $C_{22}H_{30}ClN_3O_3$ | | | |
|---|---|---|---|
| Calculated: | C, 62.92 | H, 7.20 | N, 10.00 |
| Found: | C, 62.72 | H, 7.02 | N, 9.93 |

Example 22

2-(3-Ethoxycarbonyl-6-chloro-4-quinolyl)amino-N-methyl-N-phenylacetamide; derivative No. 22. ($R_1=CH_3$; $R_2=C_6H_5$; $R_3=OC_2H_5$; $R_4=H$; $X=Cl$)
M.p. 178° C. (yield 47%).

| Analysis: $C_{21}H_{20}ClN_3O_3$ | | | |
|---|---|---|---|
| Calculated: | C, 63.40 | H, 5.07 | N, 10.56 |
| Found: | C, 63.38 | H, 5.14 | N, 10.59 |

Example 23

2-(3-Ethoxycarbonyl-6-chloro-4-quinolyl)amino-N-methyl-N-cyclohexylacetamide; derivative No. 23. ($R_1=CH_3$; $R_2=C_6H_{11}$; $R_3=OC_2H_5$; $R_4=H$, $X=Cl$)
M.p. 140° C. (yield 25%).

| Analysis: $C_{21}H_{26}ClN_3O_3$ | | | |
|---|---|---|---|
| Calculated: | C, 62.45 | H, 6.49 | N, 10.40 |
| Found: | C, 61.91 | H, 6.60 | N, 10.18 |

Example 24

2-(3-Ethoxycarbonyl-6-chloro-4-quinolyl)amino-N-methyl-N-(4-chlorophenyl)acetamide; derivative No. 24. ($R_1=CH_3$; $R_2=p-Cl-C_6H_5$; $R_3=OC_2H_5$; $R_4=H$; $X=Cl$)
M.p. 196° C. (yield 30%).

| Analysis: $C_{21}H_{19}Cl_2N_3O_3$ | | | |
|---|---|---|---|
| Calculated: | C, 58.35 | H, 4.43 | N, 9.72 |
| Found: | C, 58.20 | H, 4.29 | N, 9.66 |

Example 25

1-{2-[(3-Ethoxycarbonyl-6-chloro-4-quinolyl)amino]acetyl}piperidine; derivative No. 25.

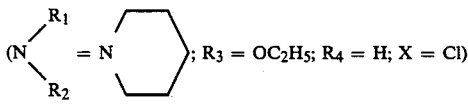

M.p. 148° C. (yield 37%).

| Analysis: $C_{19}H_{22}ClN_3O_3$ | | | |
|---|---|---|---|
| Calculated: | C, 60.72 | H, 5.90 | N, 11.18 |
| Found: | C, 60.84 | H, 5.69 | N, 11.43 |

The bis-phosphate salt of this compound was prepared. M.p. 185° C. (yield 45% from the base).

Example 26

1-{2-[(3-Ethoxycarbonyl-6-chloro-4-quinolyl)amino]acetyl}pyrrolidine, derivative NO. 26.

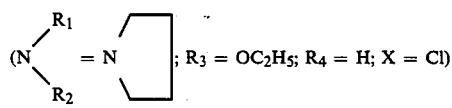

M.p. 170° C. (yield 60%).

| Analysis: $C_{18}H_{20}ClN_3O_3$ | | | |
|---|---|---|---|
| Calculated: | C, 59.75 | H, 5.57 | N, 11.61 |
| Found: | C, 59.91 | H, 5.42 | N, 11.85 |

Example 27

1-{2-[(3-Ethoxycarbonyl-6-chloro-4-quinolyl)amino]acetyl}homopiperidine; derivative No. 27.

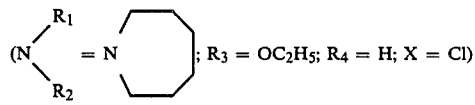

M.p. 129° C. (yield 37%).

| Analysis: $C_{20}H_{24}ClN_3O_3$ | | | |
|---|---|---|---|
| Calculated: | C, 61.61 | H, 6.20 | N, 10.78 |
| Found: | C, 61.66 | H, 6.29 | N, 10.80 |

Example 28

1-{2-[(3-Ethoxycarbonyl-6-chloro-4-quinolyl)amino]acetyl}morpholine; derivative No. 28.

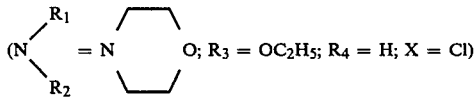

M.p. 171° C. (yield 20%).

| Analysis: $C_{18}H_{20}ClN_3O_4$ | | | |
|---|---|---|---|
| Calculated: | C, 57.22 | H, 5.34 | N, 11.12 |
| Found: | C, 57.23 | H, 5.12 | N, 11.13 |

Example 29

2-(3-Ethoxycarbonyl-6-chloro-4-quinolyl)amino-N,N-dimethylacetamide; derivative No. 29. ($R_1=R_2=CH_3$; $R_3=OC_2H_5$; $R_4=H$, $X=Cl$)
M.p. 169° C. (yield 33%).

| Analysis: $C_{16}H_{18}ClN_3O_3$ | | | |
|---|---|---|---|
| Calculated: | C, 57.23 | H, 5.40 | N, 12.51 |
| Found: | C, 57.51 | H, 5.38 | N, 12.37 |

Example 30

2-[(3-Ethoxycarbonyl-6-chloro-4-quinolyl)amino]acetamide; derivative No. 30. ($NR_1R_2=NH_2$; $R_3=OC_2H_5$; $R_4=H$; $X=Cl$)
M.p. 231° C. (yield 60%).

| Analysis: $C_{14}H_{14}ClN_3O_3$ | | | |
|---|---|---|---|
| Calculated: | C, 54.64 | H, 4.59 | N, 13.65 |
| Found: | C, 54.79 | H, 4.52 | N, 13.69 |

Example 31

2-(3-Ethoxycarbonyl-6-chloro-4-quinolyl)amino-N,N-dibutylacetamide; derivative No. 31.
($R_1=R_2=C_4H_9$; $R_3=OC_2H_5$; $R_4=H$, $X=Cl$)
M.p. 116° C. (yield 60%).

| Analysis: $C_{22}H_{30}ClN_3O_3$ | | | |
|---|---|---|---|
| Calculated: | C, 62.92 | H, 7.20 | N, 10.01 |
| Found: | C, 62.91 | H, 7.18 | N, 10.31 |

Example 32

1-{2-[(2-Ethoxycarbonyl-6-methoxy-4-quinolyl)amino]acetyl}piperidine; derivative No. 32.

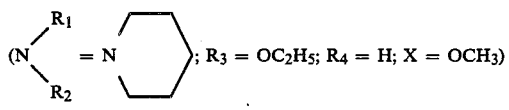

M.p. 144° C. (yield 67° C.)

| Analysis: $C_{20}H_{25}N_3O_4$ | | | |
|---|---|---|---|
| Calculated: | C, 64.67 | H, 6.78 | N, 11.31 |
| Found: | C, 64.53 | H, 6.81 | N, 11.49 |

Example 33

1-{2-[(3-Ethoxycarbonyl-6-ethoxy-4-quinolyl)amino]acetyl}piperidine; derivative No. 33.

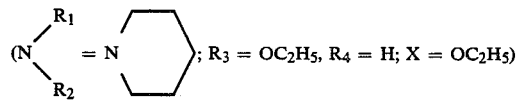

M.p. 150° C. (yield 30%).

| Analysis: $C_{21}H_{27}N_3O_4$ | | | |
|---|---|---|---|
| Calculated: | C, 65.43 | H, 7.06 | N, 10.90 |
| Found: | C, 65.38 | H, 7.26 | N, 10.86 |

Example 34

2-(3-Ethoxycarbonyl-6-chloro-4-quinolyl)amino-N,N-diisopropylacetamide; derivative No. 54.

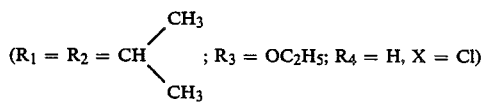

M.p. 170° C. (yield 40%).

| Analysis: $C_{20}H_{26}ClN_3O_3$ | | | |
|---|---|---|---|
| Calculated: | C, 61.30 | H, 6.69 | N, 10.72 |
| Found: | C, 61.50 | H, 6.70 | N, 10.76 |

Example 35

2-(3-Ethoxycarbonyl-6-chloro-4-quinolyl)amino-N-propyl-N-phenylacetamide; derivative NO. 35.
($R_1=C_3H_7$; $R_2=C_6H_5$; $R_3=OC_2H_5$; $R_4H$; $X=Cl$)
M.p. 147° C. (yield 35%).

| Analysis: $C_{23}H_{24}ClN_3O_3$ | | | |
|---|---|---|---|
| Calculated: | C, 64.86 | H, 5.68 | N, 9.86 |
| Found: | C, 64.78 | H, 5.63 | N, 9.75 |

Example 36

2-(3-Ethoxycarbonyl-6-chloro-4-quinolyl)amino-N-methyl-N-(2-propynyl)acetamide; derivative No. 36.
($R_1=CH_3$; $R_2=CH_2—C≡CH$; $R_3=OC_2H_5$, $R_4=H$; $X=Cl$)
M.p. 146° C. (yield 60%).

| Analysis: $C_{18}H_{18}ClN_3O_3$ | | | |
|---|---|---|---|
| Calculated: | C, 60.09 | H, 5.04 | N, 11.68 |
| Found: | C, 59.89 | H, 5.01 | N, 11.61 |

Example 37

2-(3-Ethoxycarbonyl-6-chloro-4-quinolyl)amino-N-methyl-N-benzylacetamide; derivative No. 37.
($R_1=CH_3$; $R_2=CH_2C_6H_5$; $R_3=OC_2H_5$; $R_4=H$, $X=Cl$)
M.p. 134° C. (yield 45%).

| Analysis: $C_{22}H_{22}ClN_3O_3$ | | | |
|---|---|---|---|
| Calculated: | C, 64.15 | H, 5.38 | N, 10.20 |
| Found: | C, 63.88 | H, 5.39 | N, 10.12 |

Example 38

1-{2-[(3-Ethoxycarbonyl-6-chloro-4-quinolyl)amino]acetyl}-3-methylpiperidine; derivative No. 38.

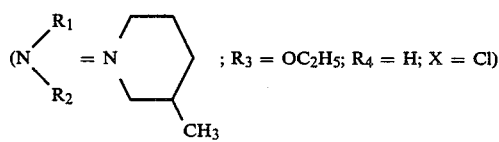

M.p. 140° C. (yield 28%).

| Analysis: $C_{20}H_{24}ClN_3O_3$ | | | |
|---|---|---|---|
| Calculated: | C, 61.61 | H, 6.20 | N, 10.78 |
| Found: | C, 61.84 | H, 6.35 | N, 10.48 |

Example 39

1-{2-[(3-Ethoxycarbonyl-6-trifluoromethyl-4-quinolyl)amino]acetyl}-3-methylpiperidine; derivative No. 39.

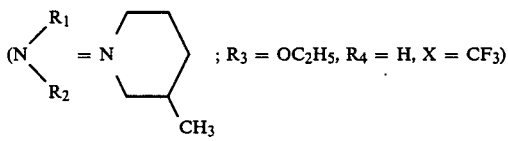

; $R_3 = OC_2H_5$, $R_4 = H$, $X = CF_3$)

M.p. 106° C. (yield 75%).

| Analysis: $C_{21}H_{24}F_3N_3O_3$ | | | |
|---|---|---|---|
| Calculated: | C, 59.57 | H, 5.71 | N, 9.92 |
| Found: | C, 59.46 | H, 5.74 | N, 9.61 |

Example 40

1-{-[(3-Ethoxycarbonyl-6-methyl-4-quinolyl)amino]acetyl}-3-methylpiperidine; derative No. 40.

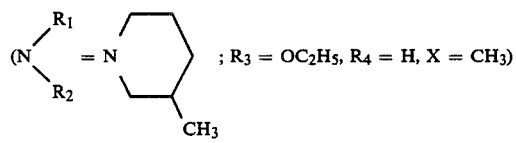

; $R_3 = OC_2H_5$, $R_4 = H$, $X = CH_3$)

M.p. 130° C. (yield 25%).

| Analysis: $C_{21}H_{27}N_3O_3$ | | | |
|---|---|---|---|
| Calculated: | C, 68.27 | H, 7.37 | N, 11.37 |
| Found: | C, 68.39 | H, 7.36 | N, 11.37 |

Example 41

2-(3-Ethoxycarbonyl-6-chloro-4-quinolyl)amino-N-methylacetamide; derivative No. 41. ($R_1=CH_3$; $R_2=H$; $R_3=OC_2H_5$; $R_4=H$; $X=Cl$)
M.p. 200° C. (yield 30%).

| Analysis: $C_{15}H_{16}ClN_3O_3$ | | | |
|---|---|---|---|
| Calculated: | C, 55.99 | H, 5.01 | N, 13.06 |
| Found: | C, 55.60 | H, 4.85 | N, 12.88 |

Example 42

2-(3-Ethoxycarbonyl-6-chloro-4-quinolyl)amino-N-propylacetamide; derivative No. 42. ($R_1=C_3H_7$; $R_2=H$; $R_3=OC_2H_5$; $R_4=H$, $X=Cl$)
M.p. 179° C. (yield 48%).

| Analysis: $C_{17}H_{20}ClN_3O_3$ | | | |
|---|---|---|---|
| Calculated: | C, 58.37 | H, 5.76 | N, 12.01 |
| Found: | C, 58.50 | H, 5.71 | N, 12.12 |

Example 43

2-(3-Carboxy-6-chloro-4-quinolyl)amino-N,N-diethylacetamide; derivative No. 43. ($R_1=R_2=C_2H_5$; $R_3=OH$; $R_4=H$; $X=Cl$)

7.6 g (0.0203 mol) of 2-(3-ethoxycarbonyl-6-chloro-4-quinolyl)amino-N,N-diethylacetamide (Example 1) and 20.3 ml (0.0203 mol) of caustic soda (N) are heated under reflux for 1 hour. After being washed with toluene, the solution is brought to pH 7 with HCl (N). The crystals obtained are filtered off, washed with water and recrystallized in a dioxane/acetic acid (8:2) mixture. The expected acid is obtained on drying: colourless crystals.
M.p. 260° C. (yield 76%).

| Analysis: $C_{16}H_{18}N_3ClO_3$ | | | |
|---|---|---|---|
| Calculated: | C, 57.23 | H, 5.40 | N, 12.51 |
| Found: | C, 57.25 | H, 5.43 | N, 12.49 |

Example 44

2-(3-Carboxy-6-methyl-4-quinolyl)amino-N,N-diethylacetamide; derivative No. 44. ($R_1=R_2=C_2H_5$; $R_3=OH$; $R_4=H$; $X=CH_3$)

2.48 g (0.0065 mol) of 2-(3-ethoxycarbonyl-6-methyl-4-quinolyl)amino-N,N-diethylacetamide hydrochloride (Example 3) in 40 ml of water and 13 ml of 2N caustic soda (0.026 mol) are brought to reflux for 2 hours. The solution is filtered at room temperature and then acidified (pH 7) with HCl (N). The expected acid precipitates: colourless crystals, m.p. >260° C. (yield 70%).

| Analysis: $C_{17}H_{21}N_3O_3H_2O$ | | | |
|---|---|---|---|
| Calculated: | C, 61.24 | H, 6.95 | N, 12.60 |
| Found: | C, 61.49 | H, 6.73 | N, 12.43. |

The following compounds were also prepared according to the process of Example 43:

Example 45

1-{2-[(3-Carboxy-6-chloro-4-quinolyl)amino]acetyl}-homopiperidine; derivative No. 45.

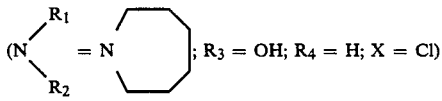

; $R_3 = OH$; $R_4 = H$; $X = Cl$)

M.p. 22 260° C. (yield 65%).

| Analysis: $C_{18}H_{20}ClN_3O_3$ | | | |
|---|---|---|---|
| Calculated: | C, 59.75 | H, 5.57 | N, 11.61 |
| Found: | C, 59.58 | H, 5.57 | N, 11.64 |

Example 46

2-(3-Carboxy-6-chloro-4-quinolyl)amino-N,N-dipropylacetamide; derivative No. 46. ($R_1=R_2=C_2H_7$; $R_3=OH$; $R_4=H$, $X=Cl$)
M.p. >260° C. (yield 42%).

| Analysis: $C_{18}H_{22}ClN_3O_3$ | | | |
|---|---|---|---|
| Calculated: | C, 59.42 | H, 6.10 | N, 11.55 |
| Found: | C, 59.18 | H, 6.21 | N, 11.26 |

Example 47

2-(3-Carboxy-6-bromo-4-quinolyl)amino-N,N-dipropylacetamide monohydrate; derivative No. 47. ($R_1=R_2=C_3H_7$; $R_3=OH$; $R_4=H$; $X=Br$)
M.p. >260° C. (yield 80%)

| Analysis: $C_{18}H_{22}BrN_3O_3$, $H_2O$ | | | |
|---|---|---|---|
| Calculated: | C, 50.71 | H, 5.67 | N, 9.85 |
| Found: | C, 50.90 | H, 5.68 | N, 10.03 |

Example 48

2-(3-Isopropyloxycarbonyl-6-chloro-4-quinolyl)amino-N,N-diethylacetamide; derivative No. 48. ($R_1=R_2C_2H_5$; $R_3=OCH(CH_3)_2$; $R_4=H$; $X=Cl$)

(1) Isopropyl 4,6-dichloroquinoline-3-carboxylate.

A solution of sodium isopropylate (0.014 mol of Na) is added dropwise at 10° C. to a solution of 4,6-dichloroquinoline-3-carbonyl chloride (0.014 mol) (prepared according to C. J. OHNMACHT et al., J. Med. Chem., 1971, 14, 1, 17–24) in dioxane (100 ml). The mixture is stirred overnight at room temperature. After evaporation of the solvents, the residue is hydrolysed. The mixture is extracted with dichloromethane and dried over sodium sulphate, and the solvent is evaporated off. The crude product is filtered on silica H with a cyclohexane/ethyl acetate (7:3) mixture. The crystals obtained are dried under vacuum.

M.p. 66° C. (yield 36%).

(2) 2-(3-Isopropyloxycarbonyl-6-chloro-4-quinolyl)amino-N,N-diethylacetamide.

A mixture of the above product (1.3 g; 0.0046 mol), 2-amino-N,N-diethylacetamide (0.84 g; 0.00506 mol) and triethylamine (1.3 ml; 0.01 mol) in ethanol (30 ml) is brought to reflux for 6 hours. After evaporation of the solvent, the residue is dissolved in dichloromethane and washed with water. After the solution has been dried over sodium sulphate and the solvent evaporated off, the crystals obtained are washed with isopropyl ether and recrystallized in an isopropyl ether/ethyl acetate (6:4) mixture: colourless crystals.

M.p. 138° C. (yield 35%).

| Analysis: $C_{19}H_{24}ClN_3O_3$ | | | |
|---|---|---|---|
| Calculated: | C, 60.39 | H, 6.40 | N, 11.12 |
| Found: | C, 60.62 | H, 6.37 | N, 11.30. |

Example 49

2-(3-Butoxycarbonyl-6-chloro-4-quinolyl)amino-N,N-diethylacetamide; derivative No. 49. ($R_1=R_2=C_2H_5$; $R_3=OC_4H_9$; $R_4=H$; $X=Cl$)

Orange crystals

M.p. 120° C.

This compound and those which follow were prepared according to the process described in Example 48.

| Analysis: $C_{20}H_{26}ClN_3O_3$ | | | |
|---|---|---|---|
| Calculated: | C, 61.30 | H, 6.69 | N, 10.72 |
| Found: | C, 61.19 | H, 6.69 | N, 10.80 |

Example 50

2-(3-Benzyloxycarbonyl-6-chloro-4-quinolyl)amino-N,N-diethylacetamide; derivative No. 50. ($R_1=R_2=C_2H_5$; $R_3=OCH_2C_6H_5$; $R_4=H$; $X=Cl$)

M.p. 146° C. (yield 36%)

| Analysis: $C_{23}H_{24}ClN_3O_3$ | | | |
|---|---|---|---|
| Calculated: | C, 64.86 | H, 5.68 | N, 9.87 |
| Found: | C, 64.70 | H, 5.73 | N, 9.87 |

Example 51

[N'-(3-Benzyloxycarbonyl-6-chloro-4-quinolyl)-N'-methylamino]-N,N-diethylacetamide; derivative No. 51. ($R_1=R_2=C_2H_5$; $R_3=OCH_2C_6H_5$; $R_4=CH_3$; $X=Cl$)

M.p. 92° C. (yield 63%).

| Analysis: $C_{24}H_{26}ClN_3O_3$ | | | |
|---|---|---|---|
| Calculated: | C, 65.52 | H, 5.96 | N, 9.55 |
| Found: | C, 65.25 | H, 5.73 | N, 9.72 |

Example 52

[N'-(3-Benzyloxycarbonyl-6-chloro-4-quinolyl)-N'-methylamino]-N,N-dipropylacetamide; derivative No. 52. ($R_1=R_2=C_3H_7$; $R_3=OCH_2C_6H_5$; $R_4=CH_3$; $X=Cl$)

M.p. 60° C. (yield 42%).

| Analysis: $C_{26}H_{30}ClN_3O_3$ | | | |
|---|---|---|---|
| Calculated: | C, 66.73 | H, 8.46 | N, 8.98 |
| Found: | C, 66.73 | H, 8.48 | N, 8.96 |

Example 53

[N'-(3-Benzyloxycarbonyl-6-methyl-4-quinolyl)-N'-methylamino]-N,N-dipropylacetamide; derivative No. 53. ($R_1=R_2=C_3H_7$; $R_3=OCH_2C_6H_5$; $R_4=CH_3$; $X=CH_3$)

Yellow oil (yield 55%).

| Analysis: $C_{27}H_{33}N_3O_3$ | | | |
|---|---|---|---|
| Calculated: | C, 72.46 | H, 7.43 | N, 9.39 |
| Found: | C, 72.13 | H, 7.74 | N, 9.49 |

Example 54

2-(3-Butyloxycarbonyl-6-chloro-4-quinolyl)-N,N-dipropylacetamide; derivative No. 54. ($R_1=R_2=C_3H_7$; $R_3=OC_4H_9$; $R_4=H$; $X=Cl$)

M.p. 111° C. (yield 25%).

| Analysis: $C_{22}H_{30}ClN_3O_3$ | | | |
|---|---|---|---|
| Calculated: | C, 62.92 | H, 7.20 | N, 10.01 |
| Found: | C, 63.00 | H, 7.26 | N, 9.98 |

Example 55

2-[3-(N-Propylcarbamoyl)-6-chloro-4-quinolyl]amino-N,N-diethylacetamide; derivative No. 55. ($R_1=R_2=C_2H_5$; $R_3=NH-C_3H_7$; $R_4=H$; $X=Cl$)

(1) 4,6-Dichloroquinoline-3-(N-propylcarboxamide).

Solutions of propylamine (3.12 ml; 0.038 mol) and triethylamine (5.3 ml; 0.038 mol) in dioxane (50 ml) are added dropwise and simultaneously at 10° C. to a solution of 4,6-dichloroquinoline-3-carbonyl chloride (0.038 mol) in dioxane (100 ml). The mixture is stirred overnight at room temperature. After evaporation of the solvent, the residue is hydrolysed and extracted with methylene chloride. After the extract has been dried over sodium sulphate and the solvent evaporated off, the crystals obtained are recrystallized in ethyl acetate.

M.p. 152° C. (yield 61%)

(2) 2-[N-Propylcarbamoyl)-6-chloro-4-quinolyl]amino-N,N-diethylacetamide.

A mixture of the above product (5.9 g; 0.0208 mol), 2-amino-N,N-diethylacetamide (3.8 g; 0.023 mol) and triethylamine (5.9 ml; 0.046 mol) in ethanol (100 ml) is brought to reflux for 3 hours. After evaporation of the solvent, the residue is solubilized in dichloromethane. After the solution has been washed with water and dried over sodium sulphate and the solvent evaporated off, the crude product is crystallized in isopropyl ether and chromatographed on a silica column with ethyl acetate. The crystals obtained are washed with isopropyl ether and recrystallized twice in an isopropyl ether/ethyl acetate (5:5) mixture: colourless crystals.

M.p. 114° C. (yield 31%).

| Analysis: $C_{19}H_{25}ClN_4O_2$ | | | |
|---|---|---|---|
| Calculated: | C, 60.55 | H, 6.69 | N, 14.87 |
| Found: | C, 60.44 | H, 6.77 | N, 14.94 |

Example 56

2-[3-(N-Phenylcarbamoyl)-6-chloro-4-quinolyl]amino-N,N-diethylacetamide; derivative No. 56. ($R_1=R_2=C_2H_5$; $R_3=NH-C_6H_5$; $R_4=H$; $X=Cl$)

Colourless crystals

M.p. 160° C. (yield 45%).

This compound was prepared according to the process described in Example 55.

| Analysis: $C_{22}H_{23}ClN_4O_2$ | | | |
|---|---|---|---|
| Calculated: | C, 64.31 | H, 5.64 | N, 13.63 |
| Found: | C, 64.31 | H, 5.42 | N, 13.46 |

Example 57

4-{2-[N-(3-Ethoxycarbonyl-6-chloro-4-quinolyl)-N-methylamino]acetyl}morpholine; derivative No. 57.

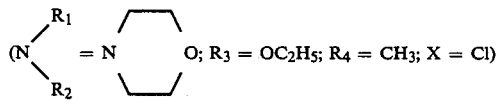

($R_1$ $R_2$ (N = N O; $R_3 = OC_2H_5$; $R_4 = CH_3$; $X = Cl$)

(1) N-(N-Benzyloxycarbonylsarcosyl)morpholine.

A mixture of 12 g (0.0219 mol) of N-benzyloxycarbonylsarcosine p-nitrophenyl ester (prepared according to A.8. MAUGER and R. WADE, J. Chem. Soc., 1965, p. 3131) and 3.8 ml of morpholine in 75 ml of ethyl acetate is stirred at room temperature for 24 h. The reaction medium is evaporated to dryness. The evaporation residue is taken up with dichloromethane. The organic phases are washed with HCl (N), NH4OH (2N) and several times with water, and then dried over anhydrous $Na_2SO_4$ and evaporated to dryness. The evaporation residue is taken up with isopropyl ether to give yellow crystals.

M.p. 82° C. (quantitative yield).

(2) N-Sarcosylmorpholine.

A mixture of 6.8 g (0.0219 mol) of the above product and 1.4 g of Pd/C (containing 10% of Pd) in 100 ml of methanol is stirred at room temperature under hydrogen for 4 h. The reaction medium is filtered on talc. On evaporation to dryness, the filtrate yields the expected amide.

(Yield 92%).

(3) 4-{2-[N-(3-Ethoxycarbonyl-6-chloro-4-quinolyl)-N-methylamino]acetyl}morpholine.

A mixture of 3.87 g (0.0143 mol) of ethyl 4,6-dichloroquinol-3-carboxylate, 3.4 g (1.5 eq.) of the above product and 3.02 ml of triethylamine in 50 ml of ethanol is heated under reflux for 5 h. The reaction medium is evaporated to dryness. The evaporation residue is taken up with dichloromethane, washed with water, dried over anhydrous $Na_2SO_4$ and then evaporated to dryness to give yellow crystals which are filtered on a silica column (ethyl acetate): yellow crystals.

M.p. 102° C. (yield 62%).

| Analysis: $C_{19}H_{22}ClN_3O_4$ | | | |
|---|---|---|---|
| Calculated: | C, 58.24 | H, 5.66 | N, 10.72 |
| Found: | C, 58.15 | H, 5.72 | N, 10.72 |

Example 58

[N'-(3-Ethoxycarbonyl-6-chloro-4-quinolyl)-N'-methylamino]-N,N-diethylacetamide; derivative No. 58. ($R_1=R_2=C_2H_5$; $R_3=OC_2H_5$; $R_4=CH_3$; $X=Cl$)

Yellow crystals

M.p. 118° C. (yield 55%).

This compound was prepared according to the process described in Example 57.

| Analysis: $C_{19}H_{24}ClN_3O_3$ | | | |
|---|---|---|---|
| Calculated: | C, 60.39 | H, 6.40 | N, 11.12 |
| Found: | C, 60.27 | H, 6.42 | N, 11.09 |

Example 59

[N'-(3-Ethoxycarbonyl-6-chloro-4-quinolyl)-N'-methylamino]-N,N-dipropylacetamide; derivative No. 59. ($R_1=R_2=C_3H_7$; $R_3=OC_2H_5$; $R_4=CH_3$; $X=Cl$)

(1) N-tert-butyloxycarbonylsarcosine.

15 g (0.0168 mol) of sarcosine, 40.3 g (0.185 mol) of $(Boc)_2O$, 168 ml (0.168 mol) of NaOH (N), 400 ml of dioxane and 200 ml of water are stirred at room temperature for 5 h. When the dioxane is removed, the residue is taken up with water. The aqueous phase is washed with dichloromethane and then acidified with HCl (6N). The mixture is extracted with dichloromethane, and the extract washed with water and dried over sodium sulphate. When the solvent has been removed, a pale yellow oil is collected (yield 89%), and this is used for the following stage.

(2) N-tert-Butyloxycarbonylsarcosine p-nitrophenyl ester.

4.13 g (1.06 eq.) of N,N'-dicyclohexylcarbodiimide is added at room temperature to a mixture of 3.6 g (0.0189 mol) of the above oil, 2.8 g (1.07 mol) of p-nitrophenol and·45 ml of ethyl acetate.

After 24 h of stirring the precipitate is filtered off. After extraction with NaOH (2N), the organic phase is washed with water and then dried. After removal of the solvent, a clear oil is collected.

(Yield 88%).

(3) 2-(N'-tert-Butyloxycarbonyl-N'-methylamino)-N,N-dipropylacetamide.

A mixture of N-tert-butyloxycarbonylsarcosine (10 g; 0.032 mol) and dipropylamine (8.8 ml; 0.064 mol) in ethyl acetate (60 ml) is stirred for 24 h at 25° LC. After addition of dichloromethane, washing with HCl (2N), NH$_4$OH (2N) and water, drying over sodium sulphate and evaporation of the solvent, the crude product is dried under vacuum (quantitative yield).

(4) 2-Methylamino-N,N-dipropylacetamide.

Trifluoroacetic acid (20 ml; 0.118 mol) is added dropwise at 5° C. to a mixture of the above product (7.7 g; 0.034 mol) in chloroform (30 ml). The solution is stirred for 2 h at room temperature. After evaporation of the solvent, the crude product is hydrolysed and extracted with ethyl ether. The aqueous phase, made alkaline, is extracted with dichloromethane and dried over sodium sulphate. After evaporation of the solvent, the crude product is dried under vacuum (yield 48%).

(5) [N'-(3-Ethoxycarbonyl-6-chloro-4-quinolyl)-N'-methylamino]-N,N-dipropylacetamide.

A mixture of ethyl 4,6-dichloroquinoline-3-carboxylate (1.7 g; 0.0097 mol), the above product (2.5 g; 0.0145 mol) and triethylamine (2.05 ml; 0.0145 mol) in ethanol (30 ml) is brought to reflux for 4 h. After evaporating the solvent, the product is taken up with dichloromethane. The organic phase is washed with water, dried and then evaporated under vacuum. The expected product is crystallized in isopropyl ether.

Colourless crystals

M.p. 76° C. (yield 33%).

| Analysis: $C_{21}H_{28}ClN_3O_3$ | | | |
|---|---|---|---|
| Calculated: | C, 62.14 | H, 6.95 | N, 10.35 |
| Found: | C, 62.29 | H, 7.25 | N, 10.40 |

Example 60

[N'-(3-Ethoxycarbonyl-6-methyl-4-quinolyl)-N'-methylamino]-N,N-diethylacetamide; derivative No. 60. ($R_1=R_2=C_2H_5$; $R_3=OC_2H_5$; $R_4=C_3$; $X=CH_3$)

Colourless crystals

M.p. 116.5° C. (yield 40%).

This compound and those which follow were prepared according to the process described in Example 59.

| Analysis: $C_{20}H_{27}N_3O_3$ | | | |
|---|---|---|---|
| Calculated: | C, 67.20 | H, 7.61 | N, 11.76 |
| Found: | C, 67.08 | H, 7.48; | N, 11.89 |

Example 61

[N'-(3-Ethoxycarbonyl-6-methyl-4-quinolyl)-N'-methylamino]-N,N-dipropylacetamide hydrochloride; derivative No. 61. ($R_1=R_2=C_3H_7$; $R_3=OC_2H_5$; $R_4=CH_3$; $X=CH_3$)

M.p. 169° C. (yield 70%).

| Analysis: $C_{22}H_{31}N_3O_3$, HCl | | | |
|---|---|---|---|
| Calculated: | C, 62.62 | H, 7.64 | N, 9.96 |
| Found: | C, 62.33 | H, 7.67 | N, 9.87 |

Example 62

[N'-(3-Ethoxycarbonyl-6-trifluoromethyl-4-quinolyl)-N'-methylamino]-N,N-dipropylacetamide; derivative No. 62. ($R_1=R_2=C_3H_7$; $R_3=OC_2H_5$; $R_4=CH_3$; $X=CF_3$)

M.p. 80° C. (yield 50%).

| Analysis: $C_{22}H_{28}F_3N_3O_3$ | | | |
|---|---|---|---|
| Calculated: | C, 60.13 | H, 6.42 | N, 9.56 |
| Found: | C, 60.13 | H, 6.70 | N, 9.24 |

Example 63

[N'-(3-Ethoxycarbonyl-6-bromo-4-quinolyl)-N'-methylamino]-N,N-dipropylacetamide; derivative No. 63. ($R_1=R_2=C_3H_7$; $R_3=OC_2H_5$; $R_4=CH_3$; $X=Br$)

M.p. 82° C. (yield 28%).

| Analysis: $C_{21}H_{28}BrN_3O_3$ | | | |
|---|---|---|---|
| Calculated: | C, 55.99 | H, 6.26 | N, 9.32 |
| Found: | C, 56.21 | H, 6.45 | N, 9.46 |

Example 64

[N'-(3-Ethoxycarbonyl-6-chloro-4-quinolyl)-N'-methylamino]-N-propylacetamide; derivative No. 64. ($R_1=C_3H_7$; $R_2=H$; $R_3=O_2H_5$, $R_4=CH_3$; $X=Cl$)

M.p. 154° C. (yield 75).

| Analysis: $C_{18}H_{22}ClN_3O_3$ | | | |
|---|---|---|---|
| Calculated: | C, 59.42 | H, 6.09 | N, 11.55 |
| Found: | C, 59.55 | H, 6.03 | N, 11.58 |

Example 65

[N'-(3-Ethoxycarbonyl-6-chloro-4-quinolyl)-N'-propylamino]-N,N-diethylacetamide; derivative No. 65. ($R_1=R_2=C_2H_5$; $R_3=OC_2H_5$; $R_4=C_3H_7$; $X=Cl$)

(1) 2-Chloro-N,N-diethylacetamide.

Solutions of diethylamine (9.15 ml; 0.0885 mol) and triethylamine (12.3 mol; 0.0885 mol) in dioxane (20 ml) are added dropwise and simultaneously at 10° C. to a solution of chloroacetyl chloride (10 g; 0.0885 mol) in dioxane (100 ml). After the mixture has been stirred overnight at room temperature and the solvent evaporated off, the residue is hydrolysed and extracted with dichloromethane. After successive washes with hydrochloric acid and 5% strength sodium bicarbonate, the extract is dried over sodium sulphate and the solvent evaporated off. The crude product is filtered on silica H with ethyl acetate (yield 61%).

(2) 2-Propylamino-N,N-diethylacetamide.

A mixture of the above product (6 g; 0.039 mol), propylamine (3.6 ml; 0.043 mol) and triethylamine (6 ml; 0.043 mol) in ethanol (60 ml) is brought to reflux for 3 h. After evaporation of the solvent, the crude product is solubilized in dichloromethane. After the solution has been washed with water and dried over sodium sulphate and the solvent evaporated off, the oil obtained is dried under vacuum (yield 56%).

(3) [N-(3-Ethoxycarbonyl-6-chloro-4-quinolyl)-N-propylamino]-N,N-diethylacetamide.

A mixture of the above product (3.7 g; 0.021 mol), ethyl 4,6-dichloroquinoline-3-carboxylate (4.9 g; 0.019 mol) and triethylamine (3 ml; 0.021 mol) in ethanol (40 ml) is brought to reflux for 3 h. After evaporation of the solvent and washing with water, the crude product is purified by chromatography on silica (cyclohexane/ethyl acetate, 5:5). The expected product is recrystallized in petroleum ether.

Yellow crystals

M.p. 85° C. (yield 30%).

| Analysis: $C_{21}H_{28}ClN_3O_3$ | | | |
|---|---|---|---|
| Calculated: | C, 62.14 | H, 6.95 | N, 10.35 |
| Found: | C, 62.19 | H, 7.12 | N, 10.25 |

Example 66

2-(3-Acetyl-6-methyl-4-quinolyl)amino-N,N-dipropylacetamide; derivative No. 66. ($R_1=R_2=C_3H_7$; $R_3=CH_3$; $R_4=H$; $X=CH_3$)

(1) 3-Acetyl-4-chloro-6-methylquinoline

3-Acetyl-4-hydroxy-6-methylquinoline (0.02 mol), prepared according to R. K. MAPARA and C. M. DESAI (CA 50 1011 b) is added to 40 ml of freshly distilled phosphorus oxychloride. The mixture is brought to reflux for 10 minutes. The solution is brought back to room temperature and then poured onto an ice/caustic soda mixture. After extraction with dichloromethane, the ogranic phase is decanted, washed until neutral, dried and concentrated. The 3-acetyl-4-chloro-6-methylquinoline (m.p. 145° C.) is used without further purification for the following stage.

(2) 2-(3-Acetyl-6-methyl-4-quinolyl)amino-N,N-dipropylacetamide 0.006 mol of 2-amino-N,N-dipropylacetamide hydrochloride and 0.013 mol of triethylamine are added to the above compound (0.006 mol) dissolved in 60 ml of absolute ethanol. This solution is brought to reflux for 12 hours. After removal of the ethanol, the residue is washed with water and then purified by chromatography on a silica column (eluant, toluene/ethanol, 95:5) and recrystallized in toluene: colourless crystals.

M.p. 163° C. (yield 75%).

| Analysis: $C_{20}H_{27}N_3O_2$ | | | |
|---|---|---|---|
| Calculated: | C, 70.35 | H, 7.97 | N, 12.31 |
| Found: | C, 70.34 | H, 7.98 | N, 12.32 |

The results of the toxicological and pharmacological trials which are reported below enabled the good tolerability of the derivatives of the invention, as well as their advantageous properties, to be demonstrated.

A further subject of the invention is consequently a drug having psychotropic activities in particular, characterized in that it contains, by way of active principle, a derivative of the formula (I) or an addition salt with a pharmaceutically acceptable inorganic or organic base or acid.

Toxicological study

The acute, chronic, sub-chronic and delayed toxicities were dealt with in this study. Performed on various animal species, the trials brought out the low toxicity and good tolerability of the derivatives of the invention.

Assessment of the acute toxicity in mice enabled it to be shown that the oral administration of doses of 1500 mg/kg of body weight was fully tolerated; for guidance, the $LD_{50}$ is 1800 mg/kg for the derivative No. 1, 1650 mg for the derivative No. 3 and 2200 for the derivative No. 43.

Pharmacological study

The results of the pharmacological trials which are reported below demonstrated the advantageous psychotropic properties of the derivatives of the invention.

These derivatives, which possess exceptional affinity for benzodiazepine receptors, have anticonvulsant, sedative, hypnotic and anxiolytic properties.

(1) Affinity for benzodiazepine receptors

This study was performed according to the technique of WASTEK et al., (Europ. J. Pharmacol., 1978, 50, 445–447) slightly modified.

Rats are sacrificed by decapitation, and the brain is removed, ground, suspended, centrifuged and resuspended.

Samples of this suspension are incubated in the presence of [$^3$H]flunitrazepam, alone or in the presence of increasing concentrations of the test compound.

The radioactivity bound on the membranes is then determined by liquid scintillation.

The concentration of product which 50% inhibits the specific binding of [$^3$H]flunitrazepam ($IC_{50}$) is thereby determined.

By way of comparison, chlordiazepoxide possesses an $IC_{50}$ (expressed in nM) of 950, and diazepam 10.

The $IC_{50}$ values determined in this manner for the derivatives of the invention are recorded below:

| Derivative | $IC_{50}$ nM | Derivative | $IC_{50}$ nM |
|---|---|---|---|
| 1 | 85 | 26 | 333 |
| 2 | 41 | 27 | 38 |
| 3 | 55 | 28 | 600 |
| 4 | 97 | 29 | 687 |
| 5 | 97 | 30 | 700 |
| 6 | 155 | 33 | 54 |
| 7 | 639 | 34 | 48 |
| 8 | 133 | 35 | 27 |
| 9 | 900 | 36 | 99 |
| 10 | 1560 | 38 | 65 |
| 12 | 16 | 41 | 440 |
| 13 | 25 | 43 | 7 |
| 14 | 17 | 44 | 46 |
| 15 | 483 | 45 | 7 |
| 16 | 38 | 46 | 1 |
| 17 | 8 | 47 | 1 |
| 18 | 26 | 48 | 69 |
| 19 | 28 | 49 | 61 |
| 20 | 40 | 50 | 27 |
| 21 | 28 | 52 | 727 |
| 22 | 14 | 53 | 638 |
| 23 | 100 | 55 | 150 |
| 24 | 251 | 56 | 136 |
| 25 | 148 | 66 | 92 |

(2) Anticonvulsant activity

The protective effect produced by the compound of the inventon against pentetrazole seizures was studied.

This test was carried out according to the method of EVERETT and RICHARDS (J. Pharm. Exp. Ther., 1944, 81, 402–407). The test products and reference products were administered orally (suspended in gum arabic) to batches of 10 mice, 30 minutes after pentetrazole (125 mg/kg subcutaneously). In each batch, the number of animals which do not show tonic seizures during the 30 minutes following the administration of the convulsant is noted. The 50% effective doses ($ED_{50}$) and the 95% confidence limits thereof were calculated by FINNEY's (1971) method.

The results are collated in the table below:

| Derivative | ED$_{50}$ (Confidence interval) (mg/kg) |
| --- | --- |
| 1 | 49 (30–88) |
| 1 maleate | 27 (18–36) |
| 5 | 50 (30–60) |
| 10 | 68 (50–90) |
| 12 | 10 (05–16) |
| 13 | 25 (13–35) |
| 14 | 40 (31–57) |
| 17 | 18 (15–22) |
| 25 | 33 (24–45) |
| 26 | 50 (27–96) |
| 29 | 38 (16–59) |
| 38 | 46 (29–70) |
| 41 | 46 (23–79) |
| 49 | 54 (36–87) |
| 52 | 31 (19–79) |
| 58 | 44 (35–56) |
| 59 | 16 (11–21) |
| 61 | 24 (14–38) |
| 63 | 24 (19–30) |
| Chlordiazepoxide | 7 |
| Phenobarbital | 10 |
| Meprobamate | 36 |

(3) Anxiolytic activity

This activity was studied by the food neophobia test. In effect, a pronounced inhibition of the feed intake can be obtained in mice when both the food and the enclosure are unfamiliar to the aninal (R. J. STEPHENS, Brit. J. Pharmacol., 1973, 47, 145 P). All anxiolytics specifically counteract neophobia phenomena.

30 minutes after oral or subcutaneous treatment with the test derivatives and the reference products, the mice, fasted for 16 to 20 hours, are isolated in a translucent enclosure and placed in the presence of an unfamiliar food for 5 minutes.

The amounts consumed are evaluated in proportion to the weight of the animal.

In each batch, the mean consumption and also the percentage variation relative to the control batch are calculated in this manner.

The results are collated in the following table:

| Derivative | Dose (mg/kg) | Route | Percentage increase |
| --- | --- | --- | --- |
| 12 | 32 | PO | 75 |
| 13 | 16 | PO | 75 |
| 17 | 32 | SC | 75 |
| 43 | 64 | SC | 75 |
| 44 | 32 | SC | 50 |
| 46 | 16 | SC | 75 |
| 58 | 64 | SC | 80 |
| 59 | 32 | PO | 146 |
| Chlordiazepoxide | 16 | PO | 73 |
| Diazepam | 4 | PO | 80 |
| Meprobamate | 60 | PO | 95 |

(4) Hypnotic activity

The hypnotic activity of the compounds of the present invention was assessed by the method of JANSEN (J. Med. Pharm. Chem., 1959, 1, 281).

After treatment i.p., each mouse is carefully placed on its back. An animal is considered to be asleep if it does not turn over and remains on its back for at least 30 sec. In each batch (10 mice per dose), the percentage of sleeping animals is noted. The 50% hypnotic dose and its 95% confidence interval were calculated according to FINNEY's (1971) method.

The results are collated in the following table:

| Derivative | 50% hypnotic dose (mg/kg) (confidence interval) | |
| --- | --- | --- |
| | i.p. | i.v. |
| 3 | 27 (22–33) | 7 (6–9) |
| 8 | 18 (13–24) | 5 (3–7) |
| 14 | 25 (21–29) | 5 (4–7) |
| 4 | 27 (21–31) | 5 (4–6) |
| 5 | 25 (21–28) | 9 (7–10) |
| 12 (Phosphate) | 38 (31–47) | 2 (1–4) |
| 12 (Sulphate) | 30 (14–39) | 6 (4–15) |
| 33 | 15 (11–19) | 5 (4–6) |
| 38 | 28 (22–37) | 9 (7–10) |

By way of comparison, the 50% hypnotic dose of thiopental sodium, a very active hypnotic agent, is 17 mg/kg, and that of midazolam is 23 mg/kg [L. PIERI et al., Arzneim. Forsch., 1981, 31(11) No. 12a, 2180–2201].

The toxicological and pharmacological studies reported above demonstrated the low toxicity of the compounds of the invention and their good tolerability, as well as their advantageous psychotropic properties which make them very useful in human and veterinary therapy.

The drug of the invention can be presented for oral administration in the form of tablets, sugar-coated tablets, capsules, drops, granules or syrup.

It can also be presented for rectal administration in the form of suppositories and for parenteral administration in the form of an injectable solution.

Each unit dose advantageously contains from 5 mg to 300 mg of active principle, and the daily administrable doses can vary from 5 mg to 500 mg of active principle, depending on the age of the patient and the severity of the condition being treated.

By way of examples without limitation, a few pharmaceutical dosage forms of the drug of the invention are given below:

1. Tablets—derivative No. 25: 30 mg

Excipient: calcium silicate, polyvinylpyrrolidone, magnesium stearate, talc, maize starch, titanium oxide, cellulose acetophthalate.

2. Sugar-coated tablets—derivative No. 12: 15 mg

Excipient: silica, starch, gelatin, magnesium stearate, shellac, talc, gum arabic, sucrose, titanium oxide.

3. Gelatin capsules—derivative No. 59: 20 mg

Excipient: talc, magnesium stearate.

4. Syrup—derivative No. 14: 300 mg

Flavoured excipient qs 100 ml

5. Injectable solution—derivative No. 8: 25 mg

Isotonic solvent qs 5 ml

6. Suppositories—derivative No. 44: 30 mg

Semi-synthetic glycerides qs 1 suppository.

The drug of the invention is used with benefit in medicine on account of its psychotropic activity.

By virtue of its anticonvulsant, sedative, hypnotic and anxiolytic properties, it is indicated both in adults and in children, in the treatment of convulsive states, anxiety states, behavioural disorders, stress and distress, and also as a muscle relaxant, hypnotic and anaesthetic.

We claim:

1. A quinolylglycinamide compound having a quinoline nucleus, said compound having the formula:

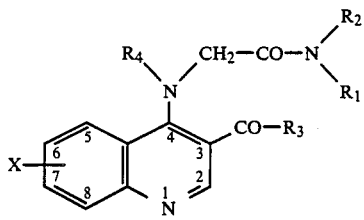 (I)

in which $R_1$ and $R_2$ are each, independently of each other, hydrogen or a lower alkyl group, or $R_1$ is an alkyl group and $R_2$ is a cyclohexyl group, a phenyl group, a benzyl group, a chlorophenyl group, or $R_1$ and $R_2$ form with the nitrogen atom to which they are directly attached a pyrrolidino, a piperidino or a homopiperidino, all of which can be substituted with a $C_1$-$C_4$ alkyl;

$R_3$ is hydrogen, a hydroxyl group, a $C_1$-$C_4$ alkyl or alkoxy group, a phenoxy group, a benzyloxy group, a phenoxy group, or a benzyloxy group, or $R_3$ denotes a group (—NH—$R_5$), in which $R_5$ is hydrogen, a lower alkyl or phenyl group;

$R_4$ is hydrogen or a lower alkyl group; and

X is is hydrogen, a halogen, a $C_1$-$C_4$ alkyl group, a cyclohexyl group, a $C_1$-$C_4$ alkoxy group, a nitro group, a trifluoromethyl group, or a methylthio group;

or the addition salts of said quinolylglycinamide compound with pharmaceutically acceptable inorganic or organic acids or, when $R_3$ denotes OH, the salts with pharmaceutically acceptable alkali metal bases or organic bases.

2. The compound of claim 1 in which $R_1$ and $R_2$ are lower alkyl groups, $R_3$ is a $C_1$-$C_4$ alkoxy group, and $R_4$ is hydrogen.

3. The compound of claim 1 in which $R_1$, $R_2$ and $R_4$ are lower alkyl groups, and $R_3$ denotes a group (—NH—$R_5$) in which $R_5$ is hydrogen or a lower alkyl group.

4. The compound of claim 1 in which $R_1$ and $R_2$ form with the nitrogen atom to which they are directly attached, a heterocyclic system selected from the group consisting of a pyrrolidino group, a piperidino group, a homopiperidino group, and a $C_1$-$C_4$ alkyl-substituted piperidino group.

5. The compound of claim 1 in which X is located at position 6 of the quinoline nucleus, and X is a halogen, a lower alkyl group, a cyclohexyl group, a $C_1$-$C_4$ alkoxy group, a nitro group or a trifluoromethyl group.

6. The compound of claim 1 in which $R_1$ and $R_2$ are propyl groups, $R_3$ is an ethoxy group, $R_4$ is hydrogen and X is chlorine at position 6 of the quinoline nucleus.

7. The compound of claim 1 in which $R_1$ and $R_2$ are propyl groups, $R_3$ is an ethoxy group, $R_4$ is a methyl group, and X is chlorine at position 6 of the quinoline nucleus.

8. A pharmaceutical composition having anticonvulsant activity comprising an anticonvulsively effective amount of a compound of claim 1 in admixture with a pharmaceutically acceptable carrier.

9. A pharmaceutical composition having anxiolytic activity comprising an anxiolytically effective amount of a compound of claim 1 in admixture with a pharmaceutically acceptable carrier.

10. A pharmaceutical composition having sedative activity comprising an sedatively effective amount of a compound of claim 1 in admixture with a pharmaceutically acceptable carrier.

* * * * *